(12) United States Patent
Kido et al.

(10) Patent No.: US 7,713,940 B2
(45) Date of Patent: May 11, 2010

(54) WATER-SOLUBLE ISOFLAVONE COMPOSITION, PROCESS FOR PRODUCING THE SAME, AND USE THEREOF

(75) Inventors: Taketoshi Kido, Ichihara (JP); Yoshihisa Iida, Ichihara (JP); Takashi Yumoto, Ichihara (JP); Toshi Miyake, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 254 days.

(21) Appl. No.: 10/556,879

(22) PCT Filed: May 19, 2004

(86) PCT No.: PCT/JP2004/006726

§ 371 (c)(1),
(2), (4) Date: Nov. 15, 2005

(87) PCT Pub. No.: WO2004/103380

PCT Pub. Date: Dec. 2, 2004

(65) Prior Publication Data

US 2006/0210607 A1  Sep. 21, 2006

(30) Foreign Application Priority Data

May 20, 2003  (JP) .............................. 2003-142602

(51) Int. Cl.
*A61K 31/7048* (2006.01)
*C07H 17/07* (2006.01)
*C07H 1/08* (2006.01)

(52) U.S. Cl. .............................. 514/28; 536/8; 536/124
(58) Field of Classification Search .................. 514/28, 514/30; 536/8
See application file for complete search history.

(56) References Cited

U.S. PATENT DOCUMENTS 4,557,927 A * 12/1985 Miyake et al. ................. 424/48
5,847,108 A * 12/1998 Kanaoka et al. ............. 536/103

FOREIGN PATENT DOCUMENTS

| JP | 62-126186 A | 6/1987 |
|----|-------------|--------|
| JP | 09-309902 A | 12/1997 |
| JP | 10-298175 A | 11/1998 |
| JP | 11-263786 A | 9/1999 |
| JP | 2000-078955 A | 3/2000 |
| JP | 2000-078956 A | 3/2000 |
| JP | 2000-327691 A | 11/2000 |
| JP | 2000-327692 A | 11/2000 |
| JP | 2002-155072 A | 5/2002 |
| JP | 2002-234844 A | 8/2002 |

OTHER PUBLICATIONS

Wang and Murphy, "Isoflavone Content in Commercial Soybean Foods", 1994, J. Agric. Food Chem., 42, p. 1666-1673.*
Pietta et al., "HPLC and MEKC determination of major flavonoids in selected food pools", 1995, Fresenius J. Anal. Chem., 352, p. 788-792.*
Piskula et al. FEBS Letters, 1999, 447, p. 287-291.*
Setchell et al. "Bioavailability of Pure Isoflavones in Healthy Humans and Analysis of Commercial Soy Isoflavone Supplements" Journal of Nutrition, 2001, 131, p. 1362S-1375S.*
Izumi et al. Journal of Nutrition, 2000, 130, p. 1695-1699.*

* cited by examiner

*Primary Examiner*—Shaojia Anna Jiang
*Assistant Examiner*—Jonathan S Lau
(74) *Attorney, Agent, or Firm*—The Webb Law Firm

(57) ABSTRACT

An isoflavone composition which contains an α-glucosyl isoflavone and isoflavone and optionally an isoflavone aglycone, wherein the ratio of the amount of aglycone in the isoflavone and the isoflavone aglycone in total to the amount of aglycone in the α-glucosyl isoflavone [(the amount of aglycone in α-glucosyl isoflavone)/(the amount of aglycone in isoflavone plus the amount of isoflavone aglycone)] is at least 2.5/1; a water-soluble isoflavone composition which contains an α-glucosyl isoflavone, isoflavone and isoflavone aglycone, wherein the ratio of the amount of isoflavone aglycone in the composition is 0.01 to 20% to the total amount of aglycone in the composition; and beverages, cosmetics, pharmaceuticals, or feeds, which contain any one of the above compositions.

7 Claims, 1 Drawing Sheet

WATER-SOLUBLE ISOFLAVONE COMPOSITION, PROCESS FOR PRODUCING THE SAME, AND USE THEREOF

BACKGROUND OF THE INVENTION

1. Field of the Invention

The present invention relates to a water-soluble isoflavone composition, its preparation and use, more particularly, to a water-soluble isoflavone composition which has an improved water-solubility, immediate activity during absorption, and sustainable physiological activity after absorption; and its preparation and use.

2. Description of the Related Art

Isoflavone and derivatives thereof (isoflavone derivatives) have been known to have an effect of preventing an excessive exudation of calcium from the bone so as not to lose supplemented calcium, and also known to prevent osteoporosis often found in elderly persons, attenuate the unbalance of female sex hormones, prevent climacteric disturbance by supplementing substances capable of functioning as a female sex hormone, inhibit the oxidation of cholesterol, prevent arteriosclerosis, and to prevent geriatric diseases such as hyperlipemia. Therefore, it has been recommended to take soybean isoflavone and derivatives thereof and various methods for extracting such compounds have been proposed.

Examples of therapeutic methods for treating the aforesaid osteoporosis with medicaments include conventional administrations of calcium agents, active vitamin $D_3$ agents, and female sex hormone agents. The onset of osteoporosis would be effectively prevented by improving daily life-style habits including meals and exercises so as not to lower the bone density. Particularly, the secretion level of estrogen, as a female sex hormone, in postmenopausal females will be lowered, resulting in an increment of risks of the onset of climacteric disturbances such as arteriosclerosis, hyperlipemia, and hypertension, as well as postmenopausal osteoporosis. Accordingly, positive intake of soybean isoflavones and derivatives thereof would be desirable as a means for preventing such diseases.

If isoflavone derivatives or compositions thereof, which are promptly absorbed by the body and kept therein at a relatively high concentration for a longer period of time, are explored, they would have a great significance.

However, there have not yet been proposed any foods or pharmaceuticals containing such a nutrient or pharmaceutical component which can be promptly absorbed by the body and then kept therein for a longer period of time and which is capable of more positively preventing the onset of osteoporosis, arteriosclerosis, and climacteric disturbances.

Therefore, if the exudation of calcium could possibly be reduced or even prevented by daily intake of foods, health foods, etc., while maintaining the bone density, preventing the onset of osteoporosis, or treating osteoporosis, then it must be highly useful. Thus, there has been desired the establishment of such a novel health food or pharmaceutical, which can easily and safely increase the bone density and prevent osteoporosis.

Similarly as above, there has been also desired the establishment of such a novel health food, pharmaceutical or cosmetic, which can attenuate the unbalance of female sex hormones, prevent climacteric disturbance by supplementing substances functioning as a female sex hormone, inhibit the oxidation of cholesterol, prevent arteriosclerosis, and prevent geriatric diseases such as hyperlipemia.

The present inventors further energetically studied on conventionally proposed methods for extracting derivatives of soybean isoflavone, methods for improving their water solubility, and products obtainable therewith.

Examples of the above methods for extracting derivatives of soybean isoflavone and for improving their water solubility are as follows:

A method comprising the steps of contacting a soybean extract with a synthetic adsorption resin to adsorb isoflavone thereupon, and eluting the adsorbed isoflavone from the resin with an organic solvent or a mixture of water and an organic solvent (Japanese Patent Laid-Open Publication No. 126,186/87);

A method for producing an isoflavone compound, comprising the steps of extracting soybean germ with a water-soluble organic solvent, concentrating the extract, and removing lipophilic components from the concentrate, followed by reconcentrating, purifying, and drying the resultant (Japanese Patent Laid-Open Publication No. 263,786/99);

A method for producing an extract of water-soluble isoflavone derivative, comprising the steps of dissolving by heating an extract of isoflavone derivative derived from soybean in ethanol solution in the presence of a branched-type maltosyl α-cyclodextrin, and removing insoluble substances from the resulting mixture after cooling (Japanese Patent Laid-Open Publication No. 2002-155,072); and A method for producing a readily water-soluble soybean isoflavone, comprising the steps of mixing a crude extract obtained from a soybean material, and removing insoluble materials from the resulting mixture after mixing with cyclodextrin in an aqueous solution (Japanese Patent Laid-Open Publication No. 298,175/98).

In addition, there has been proposed inclusion products, prepared by allowing β- or γ-cyclodextrin to include isoflavone derivatives, which have a suppressed bitterness, etc., a relatively high water solubility, and a relatively high absorption efficiency by the body (Japanese Patent Laid-Open Publication No. 309,902/97).

However, for example, the extracts obtained by the methods in Japanese Patent Laid-Open Publication Nos. 126,186/87 and 263,786/99 have a poor water-solubility as disclosed in Japanese Patent Laid-Open Publication No. 2002-155,072. Similarly, the inclusion product disclosed in Japanese Patent Laid-Open Publication No. 309,902/97 has a moot point of improving its solubility and stability in aqueous solutions.

Although the above-identified Japanese Patent Laid-Open Publication No. 2002-155,072 discloses that the method disclosed therein effectively yields an extract of isoflavone derivative, there's a moot point of improvement in terms of the yield of isoflavone and derivatives thereof due to the fact that even ethanol-soluble impurities, contained in a crude soybean extract, are exuded into a filtrate and then collected. When used after α-glucosylation in the presence of a saccharide and a saccharide-transferring enzyme, the obtained inclusion product of isoflavone or derivatives thereof should be subjected to volatilization/removal of ethanol prior to the above enzymatic modification, because ethanol contained in the inclusion product inhibits the activity of such an enzyme. As disclosed in the above-identified Japanese Patent Laid-Open Publication No. 2002-155,072, the method disclosed in Japanese Patent Laid-Open Publication No. 298,175/98 could only produce a readily water-soluble soybean isoflavone in a yield of about 10% and there's a moot point of further improvement in terms of the yield of isoflavone and derivatives thereof.

Japanese Patent Laid-Open Publication No. 2000-327,691 discloses a method for producing isoflavone derivatives derived from soybean or aglycone thereof, which comprises the steps of extracting isoflavone derivatives from soybean and/or a processed soybean product with any one of an alkaline solution with a pH of 8 or higher, hot water, or an organic solvent; allowing an α-glycosyl saccharide compound and a saccharide-transferring enzyme to act on the resulting extract to form α-glycosyl isoflavone derivatives; and removing impurities as precipitates from the resulting mixture by either adjusting the pH of the mixture to an acid pH of 5.5 or lower, or cooling the mixture.

In the method disclosed in Japanese Patent Laid-Open Publication No. 2000-327,691, the produced α-glucosyl isoflavone derivatives derived from soybean need improvement because they are relatively high in color valency and susceptible to decomposition reaction, due to the fact that they contain impurities originating from soybean other than isoflavone and derivatives thereof and have been prepared by enzymatic reaction under an alkaline condition.

Patent Document 1: Japanese Patent Laid-Open Publication No. 126,186/87
Patent Document 2: Japanese Patent Laid-Open Publication No. 263,786/99
Patent Document 3: Japanese Patent Laid-Open Publication No. 2002-155,072
Patent Document 4: Japanese Patent Laid-Open Publication No. 298,175/98
Patent Document 5: Japanese Patent Laid-Open Publication No. 309,902/97
Patent Document 6: Japanese Patent Laid-Open Publication No. 2000-327,691

BRIEF SUMMARY OF THE INVENTION

The present invention aims to provide a composition of enzymatically-modified isoflavones, i.e., an isoflavone derivative composition, which can be promptly absorbed by the body, kept therein at a relatively high concentration for a longer period of time, expected to exert effects of improving the bone density and to prevent/treat osteoporosis, used as a pharmaceutical such as an agent for improving the bone density, and capable of effectively improving the bone metabolism in a balanced manner when used in such a manner of being supplemented to food products in general, health foods, functional foods, or feeds.

The present invention aims to provide a preferable use of water-soluble isoflavone compositions such as cosmetics which are designed to positively exert the properties of such compositions.

The present invention aims to provide a process for producing enzymatically-modified isoflavones, which can produce such isoflavones in a higher yield by using, as a material, a soybean isoflavone extract containing soybean isoflavone or the like.

Figure 1:
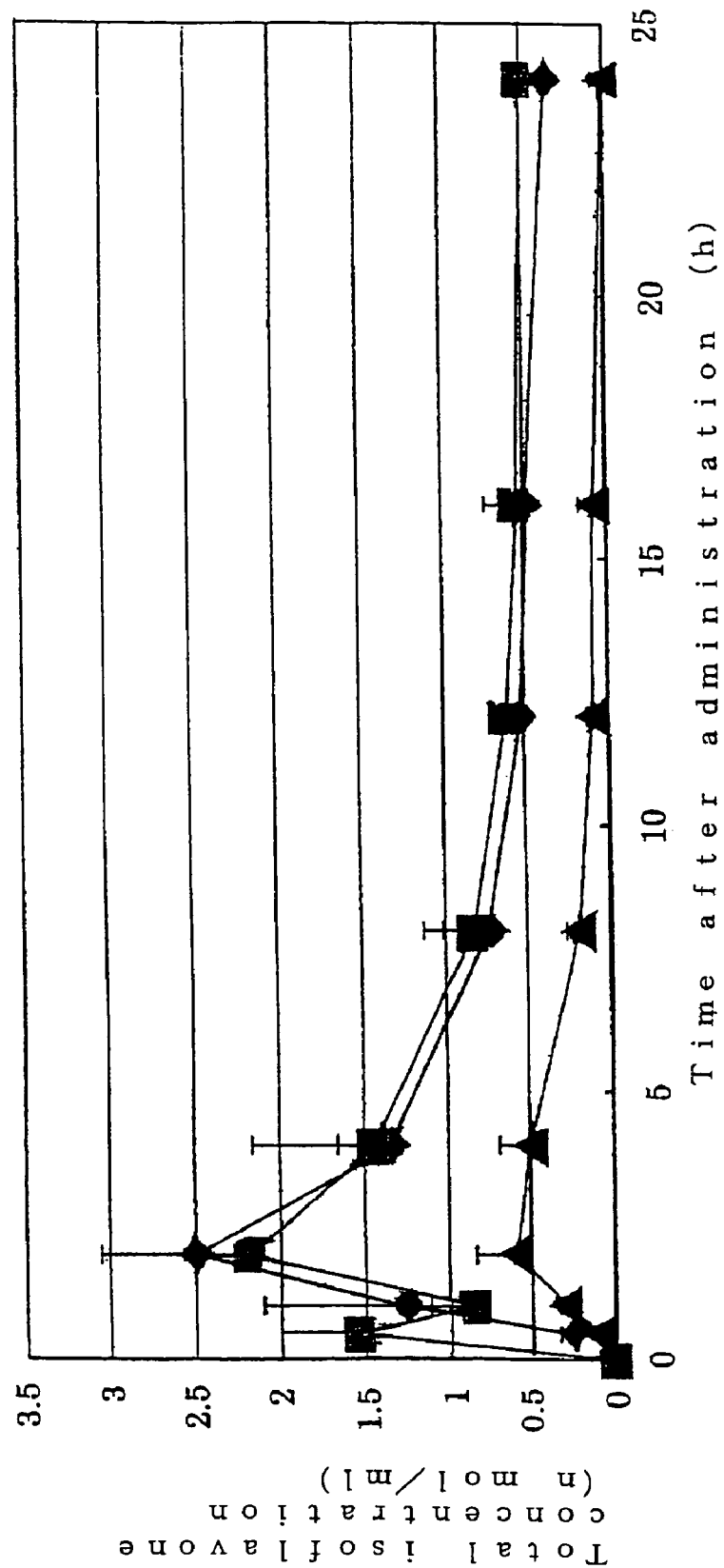
FIG. 1 is a graph for showing the relationship between the time course (h) after initiation of administration (the axis of abscissas) and the total isoflavone concentration (nmol/ml) in blood (the axis of ordinates) when a water-soluble isoflavone composition (♦), a mixture sample of "a water-soluble isoflavone composition and isoflavone aglycone" (■), and isoflavone aglycone (▲) were orally administered to test animals.

Explanation of Symbols
▲ . . . A group administered with isoflavone aglycone.
■ . . . A group administered with a mixture sample.
♦ . . . A group administered with a water-soluble isoflavone composition.

DETAILED DESCRIPTION OF THE INVENTION

The present inventors energetically studied, and as a result, they unexpectedly found that, as compared with the case of taking conventional flavonoids, when flavonoids with a specific composition ratio are taken, they stay in the body for a longer period of time so as to be expected to effectively improve the bone density and prevent/treat osteoporosis, can be used as pharmaceuticals such as agents for improving the bone density, and are expected to effectively improve the bone metabolism in a balanced manner when used by being supplemented to food products in general, health foods, functional foods, or feeds. Thus, the present inventors accomplished this invention.

The present inventors further studied for the purpose of improving the extraction efficiency of isoflavone derivatives per se which can be suitably used in preparing water-soluble isoflavone compositions, and as a result, they found that, when extracted from crude soybean extracts containing soybean isoflavone or the like, such isoflavone or the like can be effectively collected from the resulting filtrate by filtration using an alkali instead of ethanol as disclosed in Japanese Patent Laid-Open Publication No. 2002-155,072, and by precipitation of impurities in the presence of an acid after forming inclusion products by using cyclodextrin, and if necessary the separated isoflavones can be preferably used after subjected to an enzymatic modification reaction to form a water-soluble isoflavone composition or a preparation material thereof. Thus, the present inventors accomplished this invention.

Accordingly, the present invention relates to the following particulars:

The water-soluble isoflavone composition according to the present invention includes isoflavone compositions, containing an α-glucosyl isoflavone and isoflavone and optionally an isoflavone aglycone, wherein the composition has a ratio of 2.5/1 or higher, preferably, 5/1 or higher in terms of the amount of aglycone in the α-glucosyl isoflavone against the amount of aglycone contained in the isoflavone and the isoflavone aglycone [=(the amount of aglycone in α-glucosyl isoflavone)/(the amount of aglycone in isoflavone plus the amount of isoflavone aglycone)].

The water-soluble isoflavone composition according to the present invention includes an isoflavone composition containing an α-glucosyl isoflavone, isoflavone, and isoflavone aglycone, wherein the amount of isoflavone aglycone in the composition is 0.01 to 20% to the total amount of aglycone in the composition.

In the present invention, the above-identified α-glucosyl isoflavone preferably includes those which are composed of isoflavone to which an average number of 2.0 to 20 glucoses are added via the α-linkage.

In the present invention, the above-identified isoflavone composition preferably includes an α-glucosyl isoflavone, isoflavone, and isoflavone aglycone.

In the present invention, the above-identified α-glucosyl isoflavone preferably includes those which are obtained by allowing cyclodextrin and a saccharide-transferring enzyme to act on a composition containing isoflavone and an isoflavone derivative.

In the present invention, the above-identified α-glucosyl isoflavone preferably includes those which are obtained by allowing cyclodextrin to act on a composition containing isoflavone and an isoflavone derivative, cooling the resulting mixture under an acid condition, removing the formed precipitate by filtration, and allowing a saccharide-transferring enzyme to act on the filtrate.

In the present invention, β-cyclodextrin or branched β-cyclodextrin can be preferably used as cyclodextrin in any of the above-described embodiments because such β-cyclodextrins afford a desired α-glucosyl isoflavone with an improved water-solubility.

The food products, cosmetics, pharmaceuticals, or feeds according to the present invention contain any one of the above-identified water-soluble isoflavone compositions.

In the present invention, the above food products are preferably acid beverages.

In the present invention, the above food products may further contain an enzymatically-modified hesperidin and/or an enzymatically-modified rutin.

In the present invention, it is characterized in that a soybean isoflavone extract is suspended in water or an aqueous solvent, followed by adding cyclodextrin to the suspension, heating the resulting mixture to 40 to 100° C. to dissolve the added cyclodextrin, admixing the solution with an alkali, adjusting the resulting solution to give a pH of 8 to 13 to dissolve isoflavones and to allow the isoflavones to be included by cyclodextrin; and then admixing with an acid the resulting solution, containing an inclusion product of isoflavones formed by using cyclodextrin, to adjust the pH to a level of 5.5 to 2.0, lowering the temperature, removing the formed precipitate by filtration, adjusting the filtrate to give a pH of 5.0 to 7.0, and subjecting the isoflavones contained in the filtrate to an enzymatic modification.

Effect of the Invention

According to the present invention, there is provided a water-soluble isoflavone composition (an enzymatically-modified isoflavone composition), which is promptly absorbed by the body to instantly exert the desired effect, kept therein at a relatively high concentration for a longer period of time to secure a prolonged effect, expected to exert an advantageous effect on improving the bone density and on preventing/treating osteoporosis, used as pharmaceuticals such as agents for improving the bone density, and capable of effectively improving the bone metabolism in a balanced manner by being added to food products in general, health foods, functional foods, or feeds.

The present invention provides uses, where the properties of the water-soluble isoflavone composition are designed to be positively exerted, such as food products, cosmetics, pharmaceuticals, and feeds.

The present invention provides a process for producing enzymatically-modified isoflavones, which employs a step of dissolving and extracting isoflavone by using an alkali instead of dissolving such a crude soybean extract in ethanol when enzymatically-modified isoflavones are produced from a (crude) soybean isoflavone extract as a material, effectively produces enzymatically-modified isoflavones in lesser steps without employing a step of removing ethanol before enzymatic modification of isoflavones, and produces a high purity of enzymatically-modified isoflavones in a higher yield because the process does not use ethanol and this avoids contamination of ethanol-soluble impurities into the resulting extract or solution.

BEST MODE FOR CARRYING OUT THE INVENTION

The water-soluble isoflavone composition, its preparation and use according to the present invention are concretely explained as follows:

<Water-Soluble Isoflavone Composition>

The water-soluble isoflavone composition according to the present invention contains an α-glucosyl isoflavone and isoflavone and optionally an isoflavone aglycone, wherein the ratio of the amount of aglycone in the α-glucosyl isoflavone to the amount of aglycone in the isoflavone and the isoflavone aglycone in total (Cg) [=(the amount of aglycone in α-glucosyl isoflavone)/(the amount of aglycone in isoflavone plus the amount of isoflavone aglycone)] is preferably 2.5/1 or higher, in terms of the stability in an aqueous solution, immediate activity during absorption when orally taken, and medical sustainability after absorption.

The above ratio of aglycone can be expressed based on a weight ratio or a molar ratio, however, it will be expressed with the former, unless specified otherwise. In calculating the ratio of aglycone (Cg), the amount of aglycone in each α-glucosyl isoflavone, isoflavone, and isoflavone aglycone is determined with respect to genistin.

A preferable upper limit of the ratio of aglycone (Cg) is usually 25/1 or lower from a view point of that the composition with such a ratio is promptly absorbed by the body to instantly exert the desired effect, kept therein at a relatively high concentration for a longer period of time to secure a prolonged effect, expected to exert an advantageous effect of improving the bone density and preventing/treating osteoporosis, and used as pharmaceuticals such as agents for improving the bone density; and further it can effectively improve the bone metabolism in a balanced manner by being added to food products in general, health foods, functional foods, or feed.

While the ratio of aglycone (Cg) (a ratio by weight) is less than 2.5/1, the composition with such a ratio lowers in stability in solutions and is not suitably used, particularly, in liquids such as beverages.

In the present invention, as the above-identified α-glucosyl isoflavone, those which are composed of isoflavone to which an average number of 2.0 to 20 glucoses (G) are bound via the α-linkage are desirable because they can keep the stability of the isoflavone and isoflavone aglycone in the above composition in aqueous solutions.

The above isoflavone composition according to the present invention contains an α-glucosyl isoflavone and isoflavone as essential ingredients, and the preferable embodiments thereof are those which contain an α-glucosyl isoflavone, isoflavone, and isoflavone aglycone because they are promptly absorbed by the body to instantly exert the desired effect, kept therein at a relatively high concentration for a longer period of time to secure a prolonged effect, expected to exert an advantageous effect of improving the bone density, preventing/treating osteoporosis, etc., and used as pharmaceuticals such as agents for improving the bone density; and further they can effectively improve the bone metabolism in a balanced manner by being added to food products in general, health foods, functional foods, or feeds.

The above isoflavone composition according to the present invention may contain dextrins including cyclodextrins (CDs), saccharides such as oligosaccharides, proteins, peptides, and other flavonoids or the like other than the above-identified α-glucosyl isoflavone, isoflavone and optionally usable isoflavone aglycone, as long as they do not hinder the object of the present invention.

The isoflavone aglycone has the same structure as the isoflavone represented by the following Formula [I], except that $R^3$ is H (hydrogen):

TABLE 1

Formula [I]

Genin of isoflavone

Isoflavone

| Compound name | $R^1$ | $R^2$ | $R^3$ |
|---|---|---|---|
| Daidzin | H | H | Glucose (G) |
| Glycitin | H | $OCH_3$ | Glucose (G) |
| Genistin | OH | H | Glucose (G) |
| Daidzein | H | H | H |
| Glycitein | H | $OCH_3$ | H |
| Genistein | OH | H | H |

In Formula [I], $R^1$, $R^2$ and $R^3$ are defined as in the above Table 1.

In the present invention, when the number of added saccharides in an α-glucosyl isoflavone (the number of added glucoses) (n), i.e., $R^3$ in the above compound represented by Formula [I] is composed of a plurality of glucoses linked in series via the α-linkage, the number of added glucoses linked via the α-linkage is desirably an average number of 2.0 or more to improve the water-solubility of the isoflavone composition of the present invention and to keep the stability of the isoflavone and isoflavone aglycone, contained in the composition, in aqueous solutions. Although the upper limit of the number of added saccharides (n) in the α-glucosyl isoflavone is not specifically restricted, it is usually up to about 20.

To obtain isoflavone compositions with such an amount ratio of aglycone (Cg), α-glucosyl isoflavone and isoflavone and optionally usable isoflavone aglycone are mixed together to give a ratio (Cg)=[(aglycone in α-glucosyl isoflavone)/(aglycone in isoflavone plus isoflavone aglycone)] (a ratio by weight) of at least 2.5/1; or isoflavone can be subjected, for example, to α-glucosyl reaction.

Referring to the weight ratio, since the more the number of added saccharides in α-glucosyl isoflavone, the lower the ratio of the weight of aglycone per the weight of α-glucosyl isoflavone, the weight of α-glucosyl isoflavone should be needed to increase, while considering the number of added saccharides.

In the present invention, as described later, it is preferable in the case of that the above α-glucosyl isoflavone is one which is obtained by allowing cyclodextrin to act on a composition containing isoflavone and derivatives thereof, cooling the mixture under an acid condition to form a precipitate, removing the formed precipitate by filtration, allowing a saccharide-transferring enzyme to act on the filtrate containing the isoflavone and derivatives thereof at a pH of 5.0 to 7.0, where the decomposition of the isoflavone and derivatives thereof does not substantially occur, and whereby the desired α-glucosyl isoflavone and compositions thereof can be obtained in a satisfactory yield.

In the present invention, α-, β- and γ-types of cyclodextrins can be used as the above cyclodextrin. Among which, β-cyclodextrin and branched β-cyclodextrin are preferable in preparing the above compositions because they efficiently form an inclusion product of isoflavone and stabilize it.

The water-soluble isoflavone composition according to the present invention is preferably an isoflavone composition containing an α-glucosyl isoflavone, isoflavone, and isoflavone aglycone, wherein the amount of isoflavone aglycone in the composition is preferably 0.01 to 20%, more preferably, 0.5 to 10.0% to the total amount of aglycone in the composition.

The water-soluble isoflavone composition containing isoflavone aglycone in such an amount tends to have advantageous immediate- and sustainable-activities. When the amount of isoflavone aglycone is particularly lower than 0.01%, the above immediate activity tends to be defective; while the amount of isoflavone aglycone is over 20%, it tends to easily form a precipitate in a solution.

<Use (Food Products, Pharmaceuticals, etc.)>

The food products, cosmetics, pharmaceuticals or feeds (may be collectively called "food products, etc.") according to the present invention contain the above-identified water-soluble isoflavone composition.

For example, the water-soluble isoflavone composition contained in the above food products has a superior water-solubility; it dissolves in one liter of 5° C. water in an amount of one gram and has a satisfactory taste substantially free of disagreeable taste such as bitterness, puckery taste, or astringency.

The water-soluble isoflavone contained in the above food products has superior solubility in the following food products, wherein the amount to be incorporated therein is not specifically restricted but appropriately determined depending on the kinds of food products, for example, soft drinks such as water, straight juice, coffee, oolong tea, black tea, barley tea, green tea, cola drink, lemon pop, cider, milk cocoa, and cocoa; aqueous beverages such as a processed milk, fermented milk, milk product, and lactic fermenting beverage; seasonings in a liquid or semi-solid form such as miso, soy sauce, soba-tsuyu (a soup for buckwheat vermicelli), men-tsuyu (a soup for noodles), sauce for grilled meat, broth, sauce, ketchup, mayonnaise, and dressing; and water-enriched confectionery such as a jelly and pudding.

Among these food products, the water-soluble isoflavone composition superiorly dissolves, particularly, in acid beverages and it is preferably used in one liter of an acid beverage such as an citrus, apple, tomato, or pineapple juice; cola; or lactic fermenting beverage in an amount of 0.001 to 10 g of the composition.

These food products, cosmetics, pharmaceuticals or feeds may optionally contain an enzymatically-modified hesperidin and/or an enzymatically-modified rutin in an appropriate ratio to the water-soluble isoflavone composition. Food products containing the above enzymatically-modified hesperidin and water-soluble isoflavone composition or those containing the enzymatically-modified hesperidin, enzymatically-modified rutin, and the water-soluble isoflavone composition have the advantages of preventing and improving osteoporosis and of improving diseases of circulatory organs.

When orally taken, the water-soluble isoflavone composition according to the present invention is immediately absorbed by the body to exert immediate activity, kept therein at a higher concentration for a longer period of time to secure a prolonged effect, and expected to exert an advantageous effect of improving the bone density and preventing/treating osteoporosis, so that it can be used as pharmaceuticals such as prophylactic/therapeutic agents for osteoporosis, prophylactic/therapeutic agents for climacteric disturbances, and proliferation inhibitory agents for cancer cells.

As described above, when used as a pharmaceutical or health food, the water-soluble isoflavone composition can be orally taken at a dose of 0.0002 to 2 g/day/kg body weight.

The use of the water-soluble isoflavone composition by adding to food products in general, health foods, functional foods, favorite products, feeds, or quasi-drugs in an appropriate amount effectively improves the bone metabolism in a balanced manner.

More concretely, the above food products in general include, for example, confectionery, Western confectionery, frozen deserts, syrups, processed fruit products, processed vegetable products, pickles, fish meat, hams, sausages, canned foods, bottled foods, and alcoholic beverages; the above favorite products include tobaccos and gums; the above feeds include those for domestic animals and poultry, fish, and pet animals; the above cosmetics include beautifying liquids and hair dressings such as lipsticks, lipcreams, cosmetic lotions, milky lotions, and creams; and the above quasi-drugs include toothpastes.

Thus, the water-soluble isoflavone composition of the present invention can be used as an oral, external, or medical agent in the above uses and it can be further used as an additive for foods, cosmetics, and feeds.

<Preparation of Water-Soluble Isoflavone Composition>

The water-soluble isoflavone composition according to the present invention can be prepared by using a crude soybean extract (a processed product of crude soybean) such as a soybean germ, soybean powder, delipidated soybean product, soybean flour, soybean milk, and bean-curd refuse, which contain 0.05 to 0.35% by weight of soybean isoflavone or the like; or preferably it can be prepared by using a soybean isoflavone extract containing 5 to 90% by weight of isoflavone, admixing about 1 to about 200 g of the soybean isoflavone extract with one liter of water or an aqueous solvent, adding to the resulting suspension any of the aforesaid cyclodextrins, i.e., either β-cyclodextrin or branched β-cyclodextrin due to its superior solubility and economical point of view, and heating the resulting mixture to 40 to 100° C. to dissolve the cyclodextrin.

In this case, the amount of cyclodextrin used is 0.1 to 4,000 g, preferably, 1 to 2,000 g per one liter of the suspension.

After dissolving cyclodextrin in the suspension in this way, the resulting solution is admixed with an alkali to give a pH of 8 to 13, preferably, a pH of 9 to 12 to dissolve isoflavones while allowing them to form inclusion product by using cyclodextrin.

Examples of such an alkali include KOH, NaOH, and sodium hydrogen carbonate.

The inclusion of isoflavones by cyclodextrin can be confirmed by the fact that the suspension becomes transparent.

Thereafter, in the present invention, the resulting solution, containing isoflavones included by cyclodextrin, is admixed with an acid to give a pH of 5.5 to 2.0, preferably, a pH of 4.5 to 3.0, followed by decreasing the temperature usually to 1 to 60° C., preferably, 13 to 20° C. to form a precipitate. Examples of such an acid include any of organic- and inorganic-acids, such as acetic acid, hydrochloric acid, sulfuric acid, phosphoric acid, nitric acid, and citric acid.

Thereafter, the formed precipitate is removed by filtration and further enzymatically modified as indicated below to produce a water-soluble isoflavone composition:

In the present invention, the filtrate thus obtained by removing the precipitate by filtration is enzymatically modified in a usual manner after adjusted to give a pH of 5.0 to 9.0, preferably, a pH of 5.5 to 7.0 as a suitable pH condition for the enzyme activity.

As described above, the enzymatic modification of isoflavones, which has been included by cyclodextrin, results in transfer of saccharides derived from cyclodextrin to the isoflavones. As the saccharides, usually part (or the whole) of cyclodextrin, which has already formed an inclusion product of isoflavones, can be used and, in practicing the enzymatic modification, starch or partial hydrolyzates thereof and saccharides can be further added for use in the saccharide transferring.

Examples of the above enzyme include those which are capable of transferring saccharides to isoflavones without being specifically restricted, however, in the present invention, cyclodextrin glucanotransferase (CGTase) derived from the microorganisms of the genus *Bacillus* such as *Bacillus stearothermophilus* and *Bacillus macerans* can be preferably used, and among which CGTase from *Bacillus stearothermophilus* is more preferably used because of its high transglycosidation efficiency. In addition, CGTase derived from the microorganisms of the same genus *Bacillus* as above, such as *Bacillus megaterium* and *Bacillus circulans* can be used. Two or more types of such enzymes can be used in combination in the present invention. The amount of enzyme used, the conditions for enzymatic modification (temperature, volume of water, pH, time), etc., can be determined according to usual manner.

The water-soluble isoflavone composition thus enzymatically modified has a similar physiological activity as that of the intact isoflavones before enzymatic modification, and it is significantly superior in water-solubility as compared with the intact isoflavones.

The water-soluble isoflavone composition thus enzymatically modified can be fed, as one in the form of an aqueous solution of the above-mentioned enzymatically-modified isoflavones, to a non-polar porous absorption resin, which has been optionally activated, for example, with an organic solvent or an aqueous organic solvent containing 10 to 99.5% by weight of ethanol, followed by washing the resin with water, feeding the above organic solvent or the aqueous organic solvent to the resin in order to elute isoflavones adsorbed on the resin, collecting the eluate, and removing the solvent from the eluate, and then optionally freeze-drying the resultant. The treatment with such a porous absorption resin can increase "the total amount of isoflavone" (defined in later) in the enzymatically-modified isoflavones to a level of, usually, about 20 to about 80%. As the porous absorption resin, those disclosed in the column of [0009], page 4 in Japanese Patent Laid-Open Publication No. 2000-327,691, such as "DIAION™ HP", "DUOLITE™ S", and "AMBERLITE™ XAD", can be used. In place of using these porous absorption resins to increase the total amount of isoflavone, chromatographic separation can be used for such purpose.

Usually, the total amount of isoflavone in the water-soluble isoflavone composition, based on a dry solid basis, is preferably 5 to 90%, more preferably, 20 to 40% for retaining the above-identified ratio (Cg) within the desired range.

In the process for preparing the water-soluble isoflavone composition of the present invention, ethanol is not used for dissolving isoflavones to be subjected to enzymatic reaction so that a step for removing ethanol susceptible to inhibit enzyme activity can be omitted prior to the following enzymatic modification. As a result, the water-soluble isoflavone composition can be efficiently produced in fewer production steps.

Further, in the present invention, ethanol is not used in the production step for a water-soluble isoflavone composition using a soybean isoflavone extract (an extract in a solution form) so that the inflow of ethanol-soluble impurities into the extract does not occur, and thus there can be provided a process for producing water-soluble isoflavone composition which can produce α-glucosyl isoflavone in a higher yield.

It is desirable that the water-soluble isoflavone composition should contain an α-glucosyl isoflavone with an average number (n) of added saccharides of at least 2.0.

The water-soluble isoflavone composition thus obtained can be used intact or after appropriately mixed with an α-glucosyl isoflavone, isoflavone aglycone, and isoflavone so as to give the above-identified ratio of aglycone (Cg) of 2.5/1 or higher. Although the upper limit of the ratio of aglycone (Cg) should not specifically be restricted, it is usually about 25/1.

The preferred embodiments of the water-soluble isoflavone composition according to the present invention encompass those which contain an α-glucosyl isoflavone, isoflavone, and isoflavone aglycone, wherein the amount of isoflavone aglycone in the composition is, as mentioned above, preferably 0.01 to 20% to the total amount of aglycone in the composition: To adjust the amount of isoflavone aglycone within the above range, for example, conventionally known isoflavone aglycone can be added to the amount of aglycone in α-glucosyl isoflavone and isoflavone, which are contained in an enzymatically-modified isoflavone (s) to give a prescribed level, followed by alkali dissolution and pH adjustment to a desired level.

The present invention is explained in more detail with reference to the following examples but it should never be limited thereby.

Throughout the following Examples and Examples for Reference, the symbol "%" means "% by weight", unless specified otherwise.

<Measurement for the Total Amount of Isoflavone>

The total amount of isoflavone, which means the sum of isoflavone contents (unit: % by weight), in the case of an enzymatically-modified isoflavone, is measured after releasing a saccharide, which is added to an isoflavone by the action of a saccharide-transferring enzyme (CGTase), from the enzymatically-modified isoflavone by using a hydrolase (glucoamylase).

Concretely, the amount of isoflavone is quantified by dissolving one gram of an enzymatically-modified isoflavone as a sample in 0.1 liter of 25° C. water, adding 0.01 g of glucoamylase to the resulting solution, reacting the mixture at pH 5.0 and 50° C. for three hours to hydrolyze saccharides (G) linked via the α-1,4 linkage in the enzymatically-modified isoflavone, and quantifying the isoflavone using HPLC (high-performance liquid chromatography) under the following conditions, based on a conventional method, an assay for soybean isoflavone disclosed in "Kenko-Hojo-Shokuhin-Kikaku-Kijun-Shu" (A List of Standard Collection of Dietary Supplement), published by Japan Health Food & Nutrition Food Association.

HPLC Conditions:
  Apparatus: "Waters 996", commercialized by Waters;
  Column: "ODS-C18 UG120 (250 mm×4.6 mm, I.D.)", a capsule pack commercialized by Shiseido Co., Ltd.;
  Column temperature: 40° C.;
  Flow rate: 1.0 ml/min;
  Eluent: Water/methanol/acetic acid=65/30/5 (v/v/v);
  Detection: UV 254 nm; and
  Injection volume: 10 μl.

<Measurement for the Number of Added Saccharides>

Five grams of an enzymatically-modified isoflavone are dissolved in 50 ml of 25° C. deionized water, and the solution is fed to 50 ml of an adsorption resin, followed by washing the resin with water to remove substances other than α-glucosyl isoflavone. The absorption fraction is desorbed from the resin with 150 ml of 60% ethanol solution, followed by distilling off the alcohol and adding 0.01 g of glucoamylase to the resulting solution to act on it at pH 5.0 and 50° C. for five hours.

Using, as a blank solution, water similarly treated as in the above, the above glucoamylase-treated solution is quantified for glucose with a commercialized kit for determining the amount of glucose (Mutarotase/GOD method), followed by calculating the molar number (D).

While the total amount of isoflavone in the enzymatically-modified isoflavone, which has been determined by the above-identified method for the total amount of isoflavone, is expressed in terms of genistin, followed by obtaining the molar number (E).

The average number of added saccharides is determined by the following equation, where (D) is divided by (E):

Number of added saccharides=$D/E$

<Measurement for (Cg)>

After dissolving 0.05 g of Sample A in 100 ml of 25° C. deionized water, aglycone is quantified under the same conditions as used in the HPLC conditions described in the above-identified item for quantifying the total amount of isoflavone: Based on the "Method for testing soybean isoflavone" disclosed in "Kenko-Hojo-Shokuhin-Kikaku-Kijun-Shu" (A List of Standard Collection of Dietary Supplement), published by Japan Health Food & Nutrition Food Association, the isoflavone (F) and the isoflavone aglycone (G) in the sample are quantified for aglycone as genistin using a daidzin specimen as a standard specimen, wherein the amount of aglycone is determined in terms of genistin.

According to the aforesaid measurement for the total amount of isoflavone, the total amount of isoflavone in a sample is determined in terms of genistin, and the calculated value minus the above (F) and (G) values is regarded as the amount of aglycone in an α-glucosyl isoflavone.

Example 1

<Inclusion Process by Using Cyclodextrin>

Three grams of a soybean isoflavone extract containing 40% by weight of isoflavone were suspended in 600 ml of deionized water. To the suspension was added 27 g of β-cyclodextrin, and the mixture was heated to 70° C. to dissolve the β-cyclodextrin. The isoflavone was included by β-cyclodextrin in such a manner of admixing nine milliliters of a 15% aqueous sodium hydroxide solution with the above solution, and adjusting the resulting mixture to give a pH of 11.3 and to completely dissolve the isoflavone.

To the solution containing isoflavone included by β-cyclodextrin was admixed with 5.5 ml of a 20% sulfuric acid solution to adjust its pH to 4.0, and then the mixture was cooled to decrease its temperature up to 12° C.

The resulting precipitate was removed by filtration, and the filtrate was collected (may be called "Sample C").

<Reaction Procedure of Enzymatic Modification (Enzymatic Modification)>

The filtrate obtained in the above was adjusted to give a pH of 5.5 with one milliliter of 15% sodium hydroxide solution.

To 610 ml of the resulting filtrate was added a cyclomaltodextrin glucanotransferase specimen derived from *Bacillus stearothermophilus* [commercialized by Hayashibara Biochemical Laboratories Inc.; 0.3 ml] and heated overnight at 60° C. to transfer saccharides to isoflavone.

The saccharide transferring to isoflavone was confirmed by HPLC.

After completion of saccharide transferring reaction on isoflavone, the resulting reaction mixture was heated at 90° C. or over for one hour to inactivate the remaining enzyme. Thereafter, the resulting mixture was filtered. The filtrate collected was concentrated and then lyophilized to obtain 27.6 g of a dry product.

The dry product had 4.02% of "the total amount of isoflavone".

<Purification Process by Using Porous Adsorption Resin>

Then, 500 ml of a 5.5% by weight aqueous solution of the above dry product was fed to a non-polar porous adsorption resin (commercialized by Japan Organo, Co., Ltd., Model: XAD-7), which had been activated by passing therethrough 50% ethanol solution, to adsorb the isoflavones thereupon, followed by feeding 1,000 ml of water to the resin for washing and eluting/removing cyclodextrin (CD) and CD-decompositions. Thereafter, the isoflavones adsorbed on the resin were eluted therefrom by feeding 50% ethanol solution. Eluates containing isoflavones were collected and from which alcohol was distilled off, followed by lyophilizing the resulting solution to obtain 3.5 g of a solid. The total amount of isoflavones in the solid (a water-soluble isoflavone composition), called "Sample A", was 35.8%. Analysis of the solid revealed that it contained 29.2% of α-glucosyl isoflavone as isoflavone (or 18.3% as aglycone), 6.6% of isoflavone (or 4.1% as aglycone), and 0% of isoflavone aglycone; and had an average number of added saccharides of 3.6.

Example for Reference 1

<Inclusion Process by Using Cyclodextrin>

1.2 g of a soybean isoflavone extract with a total amount of isoflavone of 40% was admixed with 38 ml of an about 30% aqueous ethanol solution, and then to the resulting mixture was added 10.8 g of β-cyclodextrin, an amount equal to 9-fold volumes of the soybean isoflavone extract, followed by heating the resulting mixture at 60° C. under stirring conditions and keeping the mixture at the same temperature as above for 30 min to obtain an inclusion product of the isoflavones formed by using β-cyclodextrin.

Then, the reaction mixture was filtered after cooled to the normal temperature (25° C.). In accordance with the method in Japanese Patent Laid-Open Publication No. 2002-155,072, ethanol was distilled off from the separated filtrate, and the resulting solution was concentrated and dried to obtain 2.67 g of a solid (called "Sample B").

HPLC (high-performance liquid chromatography) analysis of the obtained solid product revealed that the total amount of isoflavone was 3.85%.

<Reaction Process for Enzymatic Modification>

Thereafter, it was needed that ethanol should have to be distilled off prior to enzymatic modification because, when an enzymatic reaction using cyclomaltodextrin glucanotransferase was proceeded using the above Sample B, the enzymatic action became lowered in a solvent system of 30% ethanol and the desired enzymatic modification scarcely progressed.

The sample (Sample C) just before the enzymatic modification in Example 1 of the present invention, which had been prepared in Example 1 by dissolving 1.2 g of a soybean isoflavone extract at a pH of 8 or over, forming an inclusion product using 10.8 g of β-cyclodextrin, readjusting the resulting solution to give a pH in the acid region, and filtering the resulting solution, was analyzed on HPLC (high-performance liquid chromatography) and revealed to have 4.12% of the total amount of isoflavone.

The total amount of isoflavone in Samples B and C were comparatively examined.

<Discussion>

(1) Comparing the total amounts of isoflavone as the results from HPLC analyses, Sample B, where an inclusion product was formed using 30% ethanol as a solvent, gave a total amount of isoflavone of 3.85%, while Sample C of the present invention gave a total amount of isoflavone of as high as 4.12%. The reason is estimable that, in the case of Sample B, ethanol-soluble impurities in the soybean isoflavone extract were flowed into the filtrate and then collected; while, in the case of Sample C, ethanol was not used in its preparation and this suppressed the contamination of impurities into the filtrate and increased the total amount of isoflavone.

(2) In Example for Reference 1, when the enzymatic modification reaction was conducted by using cyclomaltodextrin glucanotransferase, the enzymatic action in a solvent system of 30% ethanol was so lowered as to be hardly proceeded, and therefore ethanol should have to be distilled off before the enzymatic modification.

While, in Example 1 of the present invention, there exists a merit that it more facilitates the reaction processes of enzymatic modification because in which isoflavone is dissolved at a pH of 8 or over to form an inclusion product by using cyclodextrin, and the resulting mixture is adjusted to give a pH in the neutral region and then it can be subjected intact to the following enzymatic reaction without the need of distilling off ethanol.

[Test for the Dynamics in Blood]

(i) Five-week-old Sprague-Dawley (SD) male rats, having a weight of 108 to 134 g each, were purchased from Charles River Japan, Inc., and used after completion of a 7-days-quarantine.

(ii) The rats were respectively placed in a stainless-steal rat blacket cage a head per cage and bred in a breeding room controlled at a temperature of 22±3° C., a relative humidity of 50±20%, a ventilation frequency of at least 10 times/hour (an all-fresh-air-system), and a lightening time of 12 hours/day (a lightening condition of 150 to 300 luxes from 6 a.m. to 6 p.m.).

(iii) A purified feed ("AIN-76A", a solid formulation feed commercialized by Oriental Yeast Co., Ltd.) was fed to each rat using a feeding apparatus installed in each cage to allow the rats to take the feed freely since they had been received. The rats were allowed to freely take water, i.e., a city water for personal use, contained in a polycarbonated bottle for feeding water.

(iv) The rats were grouped in such a manner of evaluating their health conditions, dividing those from among the healthy rats into three groups consisting of nine heads per group by applying the randomized method to stratified animals' bodyweights to make the average weights among the groups as equal as possible. On day at the initiation of administration, the rats were 6-week-old and had a body weight in the range of 137 to 179 g.

(v) The groupings were consisted of three groups in which the rats were respectively administered with any of an enzymatically-modified isoflavone, aglycone of isoflavone, and a mixed sample with a weight ratio of aglycone of 3.6/1 ((α-glucosyl isoflavone)/(isoflavone plus aglycone of isoflavone)).

As test substances, "SoyAct™ W", a product containing 33.3% of an isoflavone aglycone commercialized by Kikkoman Corporation, was used as an aglycone of isoflavone; and "Sample A" prepared in Example 1 was used as an enzymatically-modified isoflavone.

As a mixed sample, the one prepared by dissolving Sample A and "SoyAct™ W" with an alkali and adjusting the resulting mixture to give a pH of 5.5.

"Sep-Pack C18 Cartridge", produced by Waters; which were then sequentially fed with one milliliter of 0.01M-oxalic acid and 10 ml of deionized water for washing. The substance adsorbed on each cartridge was eluted with five milliliters of 25% methanol and 10 ml of 100% methanol and then separatory collected in a test tube.

These solutions were dried in vacuo by a rotary evaporator ("EYELAN-2", commercialized by Tokyo Rikakikai Co., Ltd.). The dried products were cryopreserved at −80° C. in "SANYO DEEP FREEZER" (commercialized by Sanyo Electric Co., Ltd.), until just before analysis.

TABLE 2

Unit: % by weight
Numeral in parentheses: aglycone, based on % by weight

| Test substances | Isoflavone derivatives (in terms of isoflavone) | | | Total amount of isoflavone (%) | Weight ratio of aglycone (Cg) |
|---|---|---|---|---|---|
| | α-Glucosyl isoflavone | Isoflavone | Isoflavone aglycone | | |
| Enzymatically-modified isoflavone (aglycone (%)) | 29.2 (18.3%) | 6.6 (4.1%) | 0 (0%) | 35.8 (22.4%) | 4.5/1 |
| Aglycone of isoflavone (aglycone (%)) | 0 (0%) | 0 (0%) | 53.3 (33.3%) | 53.3 (33.3%) | 0/33.3 |
| Mixed sample (aglycone (%)) | 28.4 (17.8%) | 6.4 (4.0%) | 1.4 (0.88%) | 36.2 (22.6%) | 3.6/1 |

(vi) The test substances were respectively suspended or dissolved in a 0.5% aqueous sodium carboxymethyl cellulose (CMC-Na) solution. Using an oral sound for rat, the resulting suspension or solution was forcedly orally administered to rats, after an 18-hours-fasting, at a dose sufficient to give 50 μmol of each test substance per each rats' body weight. The rats were allowed to take only water but not any feed until collecting their blood and urine at 24 hours after the administration.

(vii) Two milliliter aliquots of blood were collected from each rat's jugular vein before the administrations of test substances (called time 0, hereinafter) and at 0.5, 1, 2, 4, 8, 12, 16 and 24 hours after the administrations; placed in plastic tubes, respectively; and centrifuged (3,500×g, at 4° C. for 10 min) by "HIGH-CAPACITY COOLING CENTRIFUGE", commercialized by Kubota Corporation, to separate plasma. At 24-hours after the administration, urine was collected from each rat, measured for volume, and centrifuged similarly as in the case of blood. The plasma and urine thus obtained were cryopreserved at −80° C. in "SANYO DEEP FREEZER", commercialized by Sanyo Electric Co., Ltd., until analysis.

(viii) A half milliliter of each of the obtained plasma and 0.5 ml of 1M-sodium acetate buffer (pH 4.5) were placed in a 1.5-ml Eppenedorf tube, sufficiently stirred, and pre-incubated at 37° C. for two minutes. Then, to each of the resulting solutions was added β-glucuronidase/sulfatase (commercialized by Sigma Chemical Company, Type-H-2; 10,500 units/ml, 4,300 units/ml) to give respective concentrations of $5.5 \times 10^2$ units/ml and $2 \times 10^2$ units/ml, followed by incubation at 37° C. for 20 min. Thereafter, the incubated solutions were instantly ice-cooled, stirred after the addition of 0.5 ml of 0.01M-oxalic acid, and then centrifuged at 8,000 rpm and 4° C. for five min. The obtained supernatants were respectively injected into (ix) In practicing HPLC analysis, the resulting residues dried in vacuo were respectively dissolved by adding thereto 100 μl of 100% methanol, and the resulting solutions were centrifuged at 15,000 rpm and 0° C. for two minutes by a centrifuge ("SIGMA KUBOTA 3615" commercialized by Kubota Corporation) to obtain samples for HPLC, followed by analysis and quantitation of the samples under the following HPLC conditions.

In this analysis, calibration curves were respectively drawn using, as standard substances, daidzein (commercialized by Kanto Chemical Co., Ltd.); and genistin (commercialized by Kanto Chemical Co., Ltd.), for quantifying these compounds; wherein the amount of daidzein was calculated by summing up daidzein and conjugates thereof, and the amount of genistin was calculated by summing up genistin and conjugates thereof. The total amount of these compounds was regarded as that of isoflavone in the blood in each rat, with the proviso that the above-identified conjugates of daidzein or genistin mean glucuronic acid or sulfuric acid conjugates of daidzein or genistin.

The results are in FIG. 1 and Table 3.

TABLE 3

| | Total amount of isoflavone in blood Concentration (nmol/ml) | | |
|---|---|---|---|
| Time (h) after initiation of administration | Enzymatically-modified specimen A | Mixed sample | Aglycone of Isoflavone |
| 0 | 0 | 0 | 0 |
| 0.5 | 0.23 | 1.54 | 0.1 |
| 1 | 1.25 | 0.85 | 0.3 |
| 2 | 2.47 | 2.18 | 0.6 |
| 4 | 1.34 | 1.45 | 0.5 |
| 8 | 0.72 | 0.84 | 0.2 |

TABLE 3-continued

| | Total amount of isoflavone in blood Concentration (nmol/ml) | | |
|---|---|---|---|
| Time (h) after initiation of administration | Enzymatically-modified specimen A | Mixed sample | Aglycone of Isoflavone |
| 12 | 0.53 | 0.63 | 0.1 |
| 16 | 0.48 | 0.54 | 0.08 |
| 24 | 0.35 | 0.51 | 0.02 |

<HPLC Conditions>

Similarly as described above;
Apparatus: "Waters 996", commercialized by Waters;
Column: "ODS-C18 UG (250 mm×4.6 mm, I.D.)", a capsule pack commercialized by Shiseido Co., Ltd.;
Column temperature: 40° C.;
Flow rate: 1.0 ml/min;
Eluent: Water/methanol/acetic acid=65/30/5 (v/v/v);
Detection: UV 254 nm; and
Injection volume: 10 µl.

<Discussion>

As evident from the results in FIG. 1 and Table 3, it can be found that the "water-soluble isoflavone compositions" and "mixtures of water-soluble isoflavone composition and isoflavone aglycone" of the present invention exhibit a higher initial concentration of the total isoflavone in blood and retain a higher concentration of the total isoflavone in blood for a relatively long period of time, compared with those of isoflavone aglycone.

[Dissolution Stability Test 1]

The ratio (Cg) of the total amount of aglycone contained in isoflavone and isoflavone aglycone to the amount of aglycone in α-glucosyl isoflavone (=[(the amount of aglycone in α-glucosyl isoflavone)/(the amount of aglycone in isoflavone plus the amount of isoflavone aglycone)] was examined in terms of their dissolution stability.

As test substances, "SoyAct™ W", (a product containing 33.3% of isoflavone aglycone, commercialized by Kikkoman Corporation), was used as an isoflavone aglycone; and "Sample A" prepared in Example 1 was used as an enzymatically-modified isoflavone.

These test substances were respectively dispersed in an adequate amount of water to give a total aglycone concentration of 250 ppm, dissolved therein at pH 12.0 with 15% sodium hydroxide, and neutralized with 20% sulfuric acid to obtain test solutions (Samples SA, SB and SC) with composition ratios (Cg) of 2.0/1, 2.5/1 and 3.0/1, respectively.

The results are in Table 4.

TABLE 4

| No. | Sample name | Starting | After two weeks | After one month | Composition ratio (Cg) |
|---|---|---|---|---|---|
| 1 | Sample SA | – | ± | ± | 2.0/1 |
| 2 | Sample SB | – | – | – | 2.5/1 |
| 3 | Sample SC | – | – | – | 3.0/1 |

In Table 4, "Composition ratio (Cg)" means "[(the amount of aglycone in α-glucosyl isoflavone)/(the amount of aglycone in isoflavone plus the amount of isoflavone aglycone)]".
The symbols in Table 4 mean: "–", with no precipitation; "±", slightly precipitated; and "+", precipitated.

[Dissolution Stability Test 2]

Considering the aspect of immediate activity, the addition of isoflavone aglycone to compositions with immediate- and sustainable-activities would be an important factor. Excessive amount thereof, however, will cause precipitation and greatly affect the shelf-life of such compositions.

Accordingly, it was examined that how the relationship between the amount of isoflavone aglycone and the total amount of aglycone in such compositions influences on precipitation during their storage for a relatively long period of time.

As test substances, "SoyAct™ W" (a product containing 33.3% of isoflavone aglycone, commercialized by Kikkoman Corporation), was used as an isoflavone aglycone, and "Sample A" prepared in Example 1 was used as an enzymatically-modified isoflavone.

These test substances were respectively dispersed in an adequate amount of water to give a total aglycone concentration of 250 ppm, dissolved therein at pH 12.0 with 15% sodium hydroxide, and neutralized with 20% sulfuric acid to obtain test solutions (Samples SD to SG) with weight ratios ((isoflavone aglycone)/(total aglycone)) of 3.0/100, 10.0/100, 20.0/100, and 30.0/100 as shown in Table 5. After 1-month storage at the normal temperature, the test solutions were examined whether they had precipitation or not.

The results are in Table 5.

TABLE 5

| No. | Sample name | Starting | After two weeks | After one month | (Isoflavone aglycone)/ (Total aglycone) |
|---|---|---|---|---|---|
| 1 | Sample SD | – | – | – | 3.0/100 |
| 2 | Sample SE | – | – | – | 10.0/100 |
| 3 | Sample SF | – | – | – | 20.0/100 |
| 4 | Sample SG | – | ± | + | 30.0/100 |

The symbols in Table 5 mean: "–", with no precipitation; "±", slightly precipitated; and "+", precipitated.

Preparation Example 1 of Food Product

<Soft Drink>

A soft drink, which had the composition in Table 6 and contained a water-soluble isoflavone composition (Cg=4.0/1 and 2.2% of isoflavone aglycone) in combination with substances capable of improving the bone density, was prepared.

TABLE 6

| Material | Content |
|---|---|
| Water | 184.81 g |
| Sugar | 6.0 g |
| Saccharide solution of fructose and glucose | 6.0 g |
| Enzymatically-modified stevia | 0.04 g |
| Concentrated lemon juice | 1.2 g |
| Lemon flavor | 0.1 g |
| Sour agent | 1.0 g |
| Enzymatically-modified hesperidin | 0.1 g |
| Water-soluble isoflavone composition | 0.01 g |
| Calcium lactate | 0.7 g |
| Vitamin C | 0.04 g |
| Vitamin $D_3$ | 150 IU |
| Vitamin K | 100 µg |
| Total | 200 g |

As described above, the combination use of the water-soluble isoflavone composition and the other ingredients capable of improving the bone density affords a soft drink which can be expected to exert effect on the maintenance and recovery of the desired bone density.

Preparation Example 2 of Food Product

<Orange Juice>

An orange juice, which had the composition in Table 7 and contained a water-soluble isoflavone composition (Cg=4.0/1 and 2.2% of isoflavone aglycone), was prepared.

TABLE 7

| Material | Content |
|---|---|
| Water | 183.36 g |
| Concentrated orange juice (concentrated into 1/6 by volume) | 10.0 g |
| Saccharide solution of fructose and glucose | 1.8 g |
| Maltitol | 4.0 g |
| Enzymatically-modified stevia | 0.04 g |
| Sour agent | 0.6 g |
| Vitamin C | 0.04 g |
| Enzymatically-modified hesperidin | 0.1 g |
| Water-soluble isoflavone composition | 0.01 g |
| Flavor | 0.05 g |
| Total | 200 g |

This product, an orange juice, can be suitably used for humans, who are anxious about osteoporosis, as a juice free of precipitation of isoflavone.

Preparation Example 3 of Food Product

<Lactic Acid Beverage>

A lactic acid beverage, which had the composition in Table 8 and contained a water-soluble isoflavone composition (Cg=4.0/1 and 2.2% of isoflavone aglycone), was prepared.

TABLE 8

| Material | Content |
|---|---|
| Water | 169.89 g |
| Lactic fermenting material | 20.0 g |
| Lemon juice | 0.8 g |
| Isomerized liquid sugar | 5.0 g |
| Maltitol | 4.0 g |
| Enzymatically-modified stevia | 0.02 g |
| Enzymatically-modified rutin | 0.08 g |
| Enzymatically-modified hesperidin | 0.1 g |
| Water-soluble isoflavone composition | 0.01 g |
| Lemon flavor | 0.1 g |
| Total | 200 g |

Although this lactic acid beverage has a low pH (acid), it can be used as one containing isoflavone free of precipitation.

Preparation Example 4 of Food Product

<Jelly>

A jelly, which had the composition in Table 9 and contained a water-soluble isoflavone composition (Cg=4.3/1 and 1.2% of isoflavone aglycone), was prepared.

TABLE 9

| Material | Content |
|---|---|
| Water | 155.026 g |
| Sugar | 20.0 g |
| Concentrated lemon juice | 17.0 g |
| Gelatinizer | 3.0 g |
| Enzymatically-modified stevia | 0.04 g |
| Sour agent | 0.4 g |
| Enzymatically-modified rutin | 0.08 g |
| Enzymatically-modified hesperidin | 0.1 g |
| Water-soluble isoflavone composition | 0.01 g |
| Gelatinizer | 3.0 g |
| Lemon flavor | 0.2 g |
| Milk basic protein | 0.4 g |
| Calcium lactate | 0.7 g |
| Gardenia yellow preparation | 0.004 g |
| Vitamin C | 0.04 g |
| Vitamin $D_3$ | 75 IU |
| Vitamin K | 50 μg |
| Total | 200 g |

Even though the product, a jelly, is a (semi-) solid, it is free of turbidity and can be used as a clear jelly containing isoflavone which does not affect the taste.

Preparation Example 1 of Cosmetic Composition

<Moisturized Cosmetic>

A slightly acidic emollient, which had the composition in Table 10 and contained a water-soluble isoflavone composition (Cg=4.3/1 and 1.2% of isoflavone aglycone), was prepared.

TABLE 10

| Material | Content |
|---|---|
| Purified water | 78.5 g |
| Glycerin | 5.0 g |
| Propylene glycol | 4.0 g |
| Oleyl alcohol | 0.1 g |
| Polyoxyethylene sorbitan monolauric acid ester | 1.5 g |
| Polyoxyethylene lauryl ether | 0.5 g |
| Ethanol | 10.0 g |
| Flavor | 0.1 g |
| Dye | q.s. |
| Antiseptic | q.s. |
| Enzymatically-modified rutin | 0.1 g |
| Enzymatically-modified hesperidin | 0.1 g |
| Water-soluble isoflavone composition | 0.1 g |
| Total | 100 g |

Preparation Example 2 of Cosmetic Composition

<Cosmetic Cream>

A cosmetic cream, which had the composition in Table 11 and contained a water-soluble isoflavone composition (Cg=4.3/1 and 1.2% of isoflavone aglycone), was prepared.

TABLE 11

| Material | Content |
|---|---|
| Beeswax | 15.3 g |
| Liquid paraffin | 76.3 g |
| Glycerin | 8.0 g |
| Enzymatically-modified rutin | 0.1 g |

TABLE 11-continued

| Material | Content |
| --- | --- |
| Enzymatically-modified hesperidin | 0.1 g |
| Water-soluble isoflavone composition | 0.1 g |
| Flavor | 0.1 g |
| Pigment | q.s. |
| Purified water | q.s. |
| Total | 100 g |

This cosmetic cream has a satisfactory stability as a cream, as well as having an activity of "preventing the retrogradation of skin" inherently exerted by isoflavone.

By replacing the composition of the cream with that of a cosmetic lotion, it can be made into a product usable as a water-soluble, stable cosmetic lotion.

BRIEF EXPLANATION OF THE
ACCOMPANYING DRAWING

[FIG. 1] FIG. 1 is a graph for showing the relationship between the time course (h) after initiation of administration (the axis of abscissas) and the total isoflavone concentration (nmol/ml) in blood (the axis of ordinates) when a water-soluble isoflavone composition (♦), a mixture sample of "a water-soluble isoflavone composition and isoflavone aglycone" (■), and isoflavone aglycone (▲) were orally administered to test animals.

The invention claimed is:

1. A water-soluble isoflavone composition, consisting essentially of an α-glucosyl isoflavone, isoflavone and isoflavone aglycone and having a total amount of an isoflavone in α-glucosyl isoflavone excluding a saccharide(s) added to the isoflavone, isoflavone and isoflavone aglycone in said water-soluble isoflavone composition being 20 to 90% based on a dry solid basis, wherein said α-glucosyl isoflavone is composed of isoflavone to which an average number of 2.0 to 20 glucoses linked in series via the α-linkage, the ratio of the amount of aglycone in said α-glucosyl isoflavone to the amount of aglycone in said isoflavone and said isoflavone aglycone in total [(the amount of aglycone in α-glucosyl isoflavone)/(the amount of aglycone in isoflavone plus the amount of isoflavone aglycone)] is 2.5/1 to 25/1, and the amount of said isoflavone aglycone in said composition is 0.5% to 20% to the total amount of aglycone in said composition.

2. The water-soluble isoflavone composition as claimed in claim 1, wherein said α-glucosyl isoflavone is obtained by allowing a saccharide-transferring enzyme to act on a soybean isoflavone extract in the presence of cyclodextrin.

3. The water-soluble isoflavone composition as claimed in claim 1, wherein said α-glucosyl isoflavone is obtained by allowing cyclodextrin to act on a soybean isoflavone extract, cooling the resulting mixture under an acid condition, removing the formed precipitate by filtration, and allowing a saccharide-transferring enzyme to act on the resulting filtrate.

4. The water-soluble isoflavone composition as claimed in claim 2, wherein said cyclodextrin is β-cyclodextrin or branched β-cyclodextrin.

5. A water-soluble isoflavone composition, consisting essentially of α-glucosyl isoflavone, isoflavone and isoflavone aglycone and having a total amount of an isoflavone in α-glucosyl isoflavone excluding a saccharide(s) added to the isoflavone, isoflavone and isoflavone aglycone in said water-soluble isoflavone composition being 20 to 90% based on a dry solid basis, wherein said α-glucosyl isoflavone is composed of isoflavone which has an average number of 2.0 to 20 glucoses linked in series via the α-linkage, the ratio of the amount of aglycone in said α-glucosyl isoflavone to the amount of aglycone in said isoflavone and said isoflavone aglycone in total [(the amount of aglycone in α-glucosyl isoflavone)/(the amount of aglycone in isoflavone plus the amount of isoflavone aglycone)] is 2.5/1 to 4.3/1, and the amount of said isoflavone aglycone in said composition is 0.5 to 20% to the total amount of aglycone in said composition.

6. A water-soluble isoflavone composition according to claim 1, wherein the total amount of isoflavone in said water-soluble isoflavone composition being 20 to 40% based on a dry solid basis.

7. A process for producing a water-soluble isoflavone composition, comprising the steps of:
  suspending a soybean isoflavone extract in water or an aqueous medium;
  adding cyclodextrin to the resulting suspension;
  heating the resulting mixture to 40 to 100° C. in order to dissolve said cyclodextrin;
  admixing the resulting solution with an alkali to adjust its pH to a level of 8 to 13 in order to dissolve isoflavones and form an inclusion product of said isoflavones by using said cyclodextrmn;
  admixing the resulting solution containing said inclusion product with an acid to adjust its pH to a level of 5.5 to 2.0;
  decreasing the temperature of the solution;
  removing the formed precipitate by filtration;
  adjusting the resulting filtrate to give a pH of 5.0 to 7.0;
  enzymatically modifying said isoflavones contained in the filtrate; and
  collecting and adjusting said isoflavones to give a water-soluble isoflavone composition consisting essentially of an α-glucosyl isoflavone, isoflavone and isoflavone aglycone and having a total amount of an isoflavone in α-glucosyl isoflavone excluding a saccharide(s) added to the isoflavone, isoflavone and isoflavone aglycone in said water-soluble isoflavone composition being 20 to 90% based on a dry solid basis, wherein said α-glucosyl isoflavone is composed of isoflavone which has an average number of 2.0 to 20 glucoses linked in series via the α-linkage, the ratio of the amount of aglycone in said α-glucosyl isoflavone to the amount of aglycone in said isoflavone and said isoflavone aglycone in total [(the amount of aglycone in α-glucosyl isoflavone)/(the amount of aglycone in isoflavone plus the amount of isoflavone aglycone)] is 2.5/1 to 25/1 , and the amount of said isoflavone aglycone in said composition is 0.5 to 20% to the total amount of aglycone in said composition.

* * * * *

UNITED STATES PATENT AND TRADEMARK OFFICE
CERTIFICATE OF CORRECTION

PATENT NO. : 7,713,940 B2
APPLICATION NO. : 10/556879
DATED : May 11, 2010
INVENTOR(S) : Kido et al.

It is certified that error appears in the above-identified patent and that said Letters Patent is hereby corrected as shown below:

In the Specification:
Column 3, delete Lines 17 through 29.

Column 21, Lines 19 through 29, delete the heading "BRIEF EXPLANATION OF THE ACCOMPANYING DRAWING" and the following paragraph.

In the Claims:
Column 22, Line 32, Claim 7, "cyclodextrmn" should read -- cyclodextrin --.

Signed and Sealed this

Twenty-fourth Day of August, 2010

David J. Kappos
*Director of the United States Patent and Trademark Office*